US005478337A

United States Patent [19]

Okamoto et al.

[11] Patent Number: 5,478,337

[45] Date of Patent: Dec. 26, 1995

[54] MEDICINE CONTAINER

[75] Inventors: Hideshi Okamoto; Yoshiki Maesaki; Hidekatsu Shoji, all of Tokushima; Isamu Tateishi, Naruto; Takayuki Hagiwara; Tetsuya Hatono, both of Suita, all of Japan

[73] Assignees: Otsuka Pharmaceutical Factory, Inc., Naruto; Takeda Chemical Industries, Ltd., Osaka, both of Japan

[21] Appl. No.: 167,793

[22] PCT Filed: Apr. 28, 1993

[86] PCT No.: PCT/JP93/00561

§ 371 Date: Dec. 20, 1993

§ 102(e) Date: Dec. 20, 1993

[87] PCT Pub. No.: WO93/21891

PCT Pub. Date: Nov. 11, 1993

[30] Foreign Application Priority Data

| | | | |
|---|---|---|---|
| May 1, 1992 | [JP] | Japan | 4-029159 U |
| Mar. 10, 1993 | [JP] | Japan | 5-010135 U |

[51] Int. Cl.$^{6}$ .................... A61B 19/00

[52] U.S. Cl. .................... 604/413; 604/56; 604/82; 604/87; 604/89; 604/403; 604/408; 604/415; 604/416

[58] Field of Search .................... 604/403, 407–408, 604/411–416, 905, 56, 82, 87–92; 128/912, DIG. 24; 215/254–256; 220/265, 266, 270

[56] References Cited

U.S. PATENT DOCUMENTS

| | | | |
|---|---|---|---|
| 4,583,971 | 4/1986 | Bocquet et al. . | |
| 4,936,841 | 6/1990 | Aoki et al. | 604/413 |
| 5,086,780 | 2/1992 | Schmitt | 604/403 |
| 5,342,346 | 8/1994 | Honda et al. | 604/413 |
| 5,364,386 | 11/1994 | Fukuoka et al. | 604/414 |

FOREIGN PATENT DOCUMENTS

| | | |
|---|---|---|
| 0565103 | 4/1993 | European Pat. Off. . |
| 63-135642 | 9/1988 | Japan . |
| 2-86536 | 7/1990 | Japan . |
| 3-37067 | 2/1991 | Japan . |

*Primary Examiner*—Randall L. Green
*Assistant Examiner*—P. Zuttarelli
*Attorney, Agent, or Firm*—Armstrong, Westerman, Hattori, McLeland & Naughton

[57] ABSTRACT

An outer tube having a double-ended needle accommodated therein upwardly and downwardly slidably is hermetically, removably but fixedly joined to an opening seal portion of a dissolving liquid container. An inner tube having a medicine-containing vial accommodated therein in an inverted state is joined to an upper end of the outer tube so as to be movable from a joined position of shallow fit to a joined position of deep fit. The joint between the outer and inner tubes is provided with a seal ring for holding the interior of the tubes airtight and a restraining mechanism for holding the inner tube in the joined position of shallow fit. The medicine container thus constructed is excellent in impact resistance and shakeproofness for transport and storage, usable by a facilitated mixing procedure for preparing a medicinal solution, simple in overall structure and disposable as separated into components after use.

12 Claims, 12 Drawing Sheets

MEDICINE CONTAINER

TECHNICAL FIELD

The present invention relates to medicine containers which comprise a container having an antibiotic or like medicine hermetically accommodated therein and another container joined thereto and similarly containing a liquid for dissolving the medicine, such that when the medicine is to be administered to the patient as by drip infusion, the two component containers are caused to aseptically communicate with each other to mix the contents together into a solution.

BACKGROUND ART

Research has been conducted on various medicine containers of the type described, which include those having a double-ended needle. These containers have the advantage of being usable for medicines as contained in conventional vials and not permitting ingress of broken fragments of such as rubber closures used in the vial into the dissolving solution. Some of the containers of the same type already proposed have the structure disclosed in Unexamined Japanese Utility Model Publication SHO 63-135642 (see FIGS. 6 to 8 in particular) or in Unexamined Japanese Patent Publication HEI 2-1277. The medicine container of the former publication has the advantage of being simple in structure and disposable as divided into components, but still remains to be improved in construction for the ease of mixing procedure and has the likelihood of peel paper separating off, for example, during transport. The medicine container of the latter, although free of the problem of the former container, has the problem of being complex in structure, costly to make and not disposable as separated into components. Thus, the proposed containers have both merits and demerits.

DISCLOSURE OF THE INVENTION

The main object of the present invention is to provide a medicine container which is excellent in impact resistance and shakeproofness for transport and storage, usable through a facilitated mixing procedure for preparing a medicinal solution, simple in overall construction and disposable as separated into components after use.

Other features of the present invention will become apparent from the following description.

The present invention provides a medicine container characterized in that the container comprises:

(a) a dissolving liquid container having an opening seal portion at an upper end thereof, (b) an outer tube removably hermetically joined and secured to the opening seal portion of the dissolving liquid container so as to extend upward from the opening seal portion concentrically therewith, (c) a double-ended needle fitted in the outer tube and slidable upward and downward, the needle being usually held in an upper position above the opening seal portion and movable from the upper position to a lower position to pierce the seal portion for use, (d) an inner tube slidably fitted in the outer tube through an open upper end thereof and usually held in a first joined position of shallow fit, the inner tube being movably from the first joined position to a second joined position of deep fit for use, (e) a medicine-containing vial fixedly accommodated removably in an inverted state in the inner tube with an opening seal portion of the vial directed downward, the vial being positioned above the needle in the upper position when the inner tube is in the first joined position and movable with the movement of the inner tube to a position where the opening seal portion of the vial is pierced by the needle in the lower position when the inner tube moves to the second joined position, (f) restraining means provided in a joint between the outer tube and the inner tube for usually restraining the inner tube in the first joined position relative to the outer tube and releasing the inner tube from the restrained position for use, and (g) a seal ring provided in the joint between the outer tube and the inner tube for holding the joint hermetic.

The inner tube and the outer tube can be reliably held joined together as predetermined with good stability by the restraining mechanism provided on the joint between the inner tube and the outer tube while the medicine container of the invention is being transported. Furthermore, the medicine and the liquid packaged in the medicine container can be mixed together easily by forcing the inner tube into the outer tube. After a solution has been prepared by the mixing procedure, it is possible to separate the dissolving liquid container from the outer tube at the joint therebetween, to separate the inner tube from the outer tube by withdrawing the inner tube therefrom and, when required, to withdraw the double-ended needle and the vial from the inner and outer tubes.

BEST MODE OF CARRYING OUT THE INVENTION

Different embodiments of the present invention will be described below with reference to the accompanying drawings.

FIGS. 1 to 7 show a first embodiment of the invention. According to the first embodiment, the medicine container of the invention comprises a dissolving liquid container A, outer tube B, double-ended needle C, inner tube D, medicine-containing vial E, restraining mechanism F and/or restraining mechanism F', seal ring G and adapter H as shown in overall views of FIGS. 1 and 2.

The dissolving liquid container A comprises a body 1 having an open upper end, and an opening seal portion 2 closing the opening.

The body 1 is deformable by pressing, and molded of a thermoplastic synthetic resin such as polyethylene or polypropylene and has a dissolving liquid 3 accommodated therein.

Figure 2:
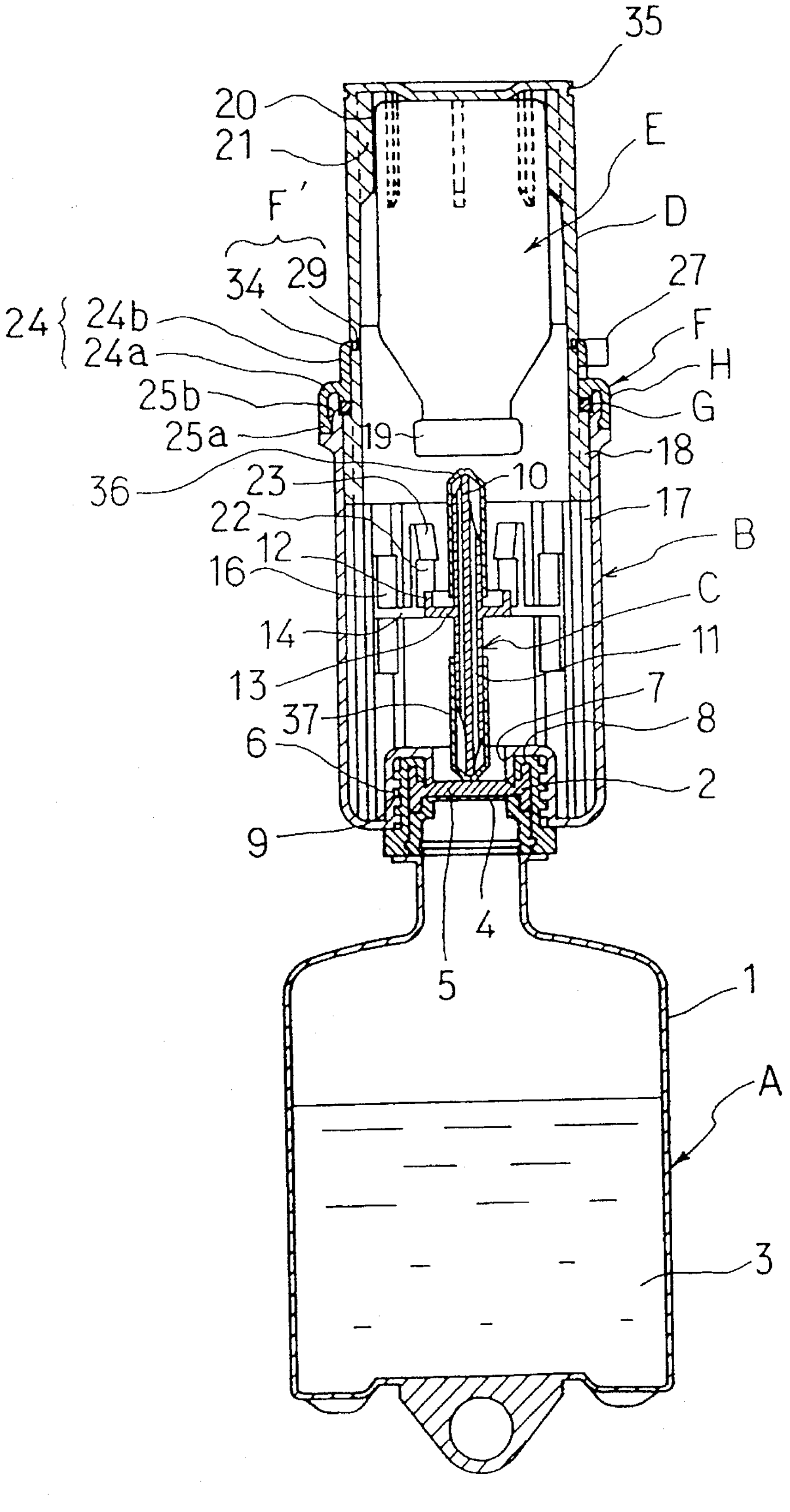
FIG. 2 is an enlarged side elevation in vertical section of the same.

The opening seal portion 2 can be composed of an inner closure 4 of plastics attached to the open upper end of the body 1 as by heat sealing, and a rubber closure 5 resembling a cap and fitted over the inner closure as will be apparent from FIG. 2. The opening seal portion 2 is not limited specifically in structure insofar as it permits piercing with a needle member of the double-ended needle C.

The outer tube B is made of plastics and fixedly joined to the seal portion 2 of the container A so as to extend upward from the portion 2 concentrically therewith while holding the needle C therein upwardly and downwardly slidable.

The outer tube B has a socket 6 upwardly projecting from its lower end concentrically therewith as means for fixedly joining the tube to the seal portion 2. When the socket 6 is fastened to the seal portion 2 by being guided by a threaded portion 9, an engagement ring 7 inwardly projecting from the upper end of the socket 6 and inverted L-shaped in section is brought into engagement and intimate contact with an annular projection 8 on the top surface of the seal portion 2 along its outer periphery, with the lower end of the ring 7 pressed against the top surface of the rubber closure 5, whereby a seal is formed to provide an airtight joint.

The double-ended needle C is made of plastics and comprises a pair of upper and lower needle members 10 and 11 communicating with each other. The needle members 10, 11, which are of the two-channel type as illustrated, can alternatively be of the single-channel type, and are fixed to a disklike needle holder 13 in alignment with its center axis. The holder is reinforced with an upwardly projecting ridge 12. The needle holder 13 has a plurality of arms radially extending from the outer periphery thereof, for example, four arms 14 arranged at a spacing of 90 degrees (see FIG. 3). Each of the arms 14 is formed at its outer end with a slider 16 having an enlarged frictionally engaging surface and in contact with the inner peripheral surface of the outer tube B. The holder 13 usually holds the needle C in an upper position above the seal portion 2. When subjected to a depressive force greater than the force of frictional engagement, the needle C is moved inside the outer tube B from the upper position to a lower position (see FIG. 7) where the needle pierces the opening seal portion 2. To guide this movement, the guide grooves 15 (see FIG. 3) is formed on the inner peripheral surface of the outer tube B, the guide grooves 15 extending vertically over the entire length thereof for the sliders 16 at the outer ends of the arms 14 to engage in. The needle C can be held in position also by small protrusions (not shown) formed on the inner surface of the outer tube B for engaging the sliders 16.

Figure 3:
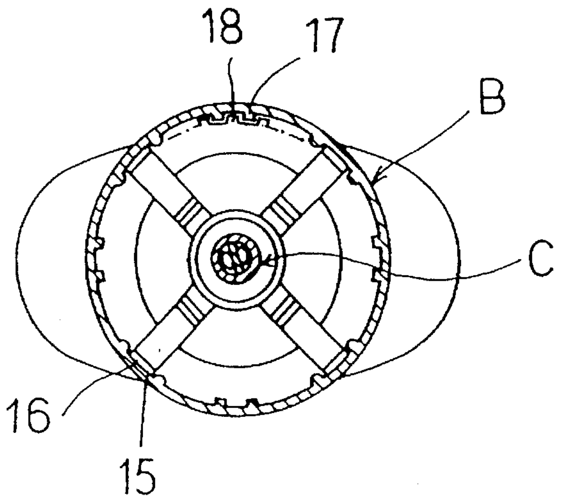
FIG. 3 is a view in section taken along the line 3—3 in FIG. 1.
Figure 7:
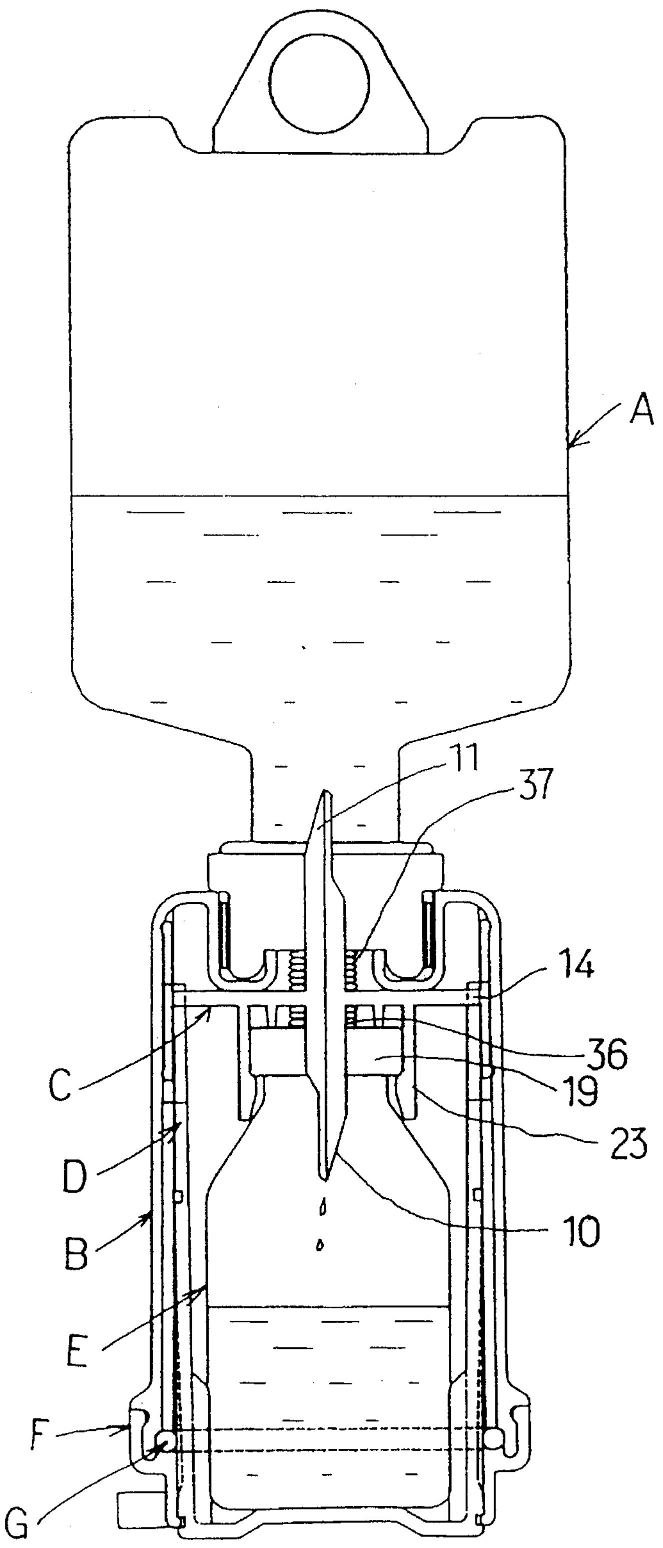
FIG. 7 is a diagram for illustrating the first embodiment in use.

The inner tube D is in the form of a tube of plastics having a closed upper end but no bottom, and is slidably fitted in the outer tube B through an open upper end thereof so as to be movable from a first joined position of shallow fit (see FIG. 2) to a second joined position of deep fit (see FIG. 7). To permit the inner tube D to move from the first joined position to the second joined position without rotation, furrow-defining engaging ridges 17 and 18 can be formed respectively on the inner peripheral surface of the outer tube B over the entire length thereof and on the outer peripheral surface of lower portion of the inner tube D as shown in FIG. 2. FIG. 3 schematically shows the ridges 17, 18 in engagement with each other.

As shown in FIG. 2, the medicine-containing vial E is fixedly but removably held in an inverted state in the inner tube D with an opening seal portion 19 of the vial directed downward. The vial is fixedly held to the inner tube by suitable means. For example, the inner peripheral surface of the inner tube D defining an insertion space 20 can be formed at its upper portion with a multiplicity of platelike engaging rims 21 integrally with the tube D, such that the lower portion of the vial E is forced into the space 20 against the inherent elasticity of the rims 21. The opening seal portion 19 of the vial E comprises, for example, a rubber closure to permit piercing with the double-ended needle C. Like the seal portion 2 of the container A, the seal portion 19 may comprise a rubber closure and a plastics closure in combination.

The arms 14 of the needle C can each be provided with a hook piece 22 for fixedly holding the opening seal portion 19 upon the inner tube D moving to the second joined position (see FIG. 7). The hook piece 22 has on the inner side of its upper portion a hook 23 having a slanting front face. While holding the seal portion 19, the hook 23 is in engagement with a rear part of the seal portion 19, preventing this portion from slipping off. To permit the hook 23 to engage the seal portion 19, the hook piece 22 is outwardly tiltable suitably against its inherent elasticity.

The outer and inner tubes B, D have therebetween a joint provided with the aforementioned adapter H which is made of plastics and which has the restraining mechanisms F and F' for holding the inner tube D in the first joined position of shallow fit.

The adapter H comprises a tubular body 24 having a lower portion **24*a* which is fitted around the upper end of the outer tube B. When thus fitted, the adapter H is fixed in position by elastic engagement between projecting and recessed engaging portions 25*a*, 25*b*. The adapter is removable from the outer tube B by bringing the projecting and recessed portions 25*a*, 25*b*** out of elastic engagement with each other.

The body 24 has an upper portion **24*b* which is freely fitted around the outer periphery of the inner tube D in the first joined position and which has a cut 26 (see FIG. 1) at a circumferentially intermediate part thereof. One cut end 26*a* of the portion 24*b* defining the cut 26 is integral with a manual lever 27** serving as one component of the restraining mechanism F.

Figure 5:
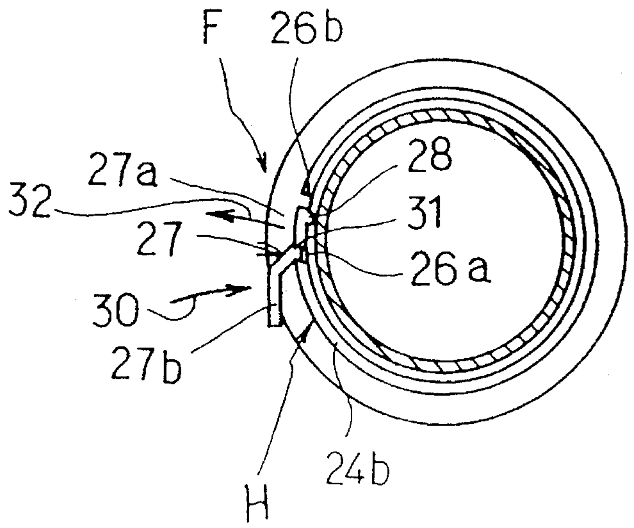
FIG. 5 is a diagram for illustrating a restraining mechanism F included in the first embodiment.

As shown in FIG. 5, the lever 27 has an inward portion 27*a* extending from the cut end 26*a* toward the other cut-defining end 26*b* of the portion 24*b* along the outer periphery of the inner tube D, and an outward portion 27*b* extending in a direction opposite to the inward portion 27*a* progressively outwardly away from the outer periphery of the upper portion 24*b*.

Figure 6:
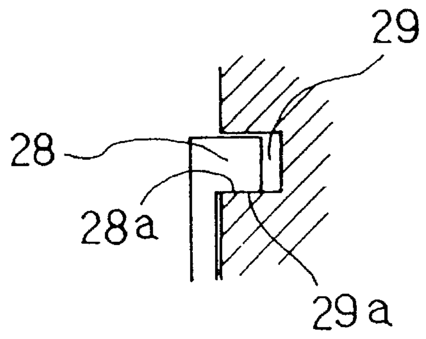
FIG. 6 is a diagram for illustrating a restraining mechanism F' in the same.

A pawl 28 which is substantially flat at its top is formed at the outer end of inward portion 27*a* of the manual lever 27 on the inner side thereof. The inner tube D is formed in its outer peripheral surface with an annular engaging recessed portion 29 opposed to the pawl 28 and serving as another component of the restraining mechanism F. The pawl 28 usually engages in the recessed portion 29 elastically, holding the inner tube D in the first joined position. However, when the outward portion 27*b* of the lever 27 is pressed toward the direction of arrow 30 (see FIG. 5), the inward portion 27*a*, as supported at an intermediate point 31 for pivotal movement, opens toward the direction of arrow 32 against inherent elasticity, disengaging the pawl 28 from the recessed portion 29 to thereby release the inner tube D from the restrained position. FIG. 6 shows the pawl 28 elastically engaging in the recessed portion 29 while restraining the inner tube. Since the pawl 28 has a flat lower face 28*a* in face-to-face engagement with the lower wall 28*a* of the recessed portion 29, the tube D can be firmly held in the first joined position.

An engaging projecting portion 34 semicircular in section and projecting inward can be formed at the upper end of inner peripheral surface of the body upper portion 24*b* of the adapter H. The projecting portion 34 engages in the recessed portion 29 in the outer peripheral surface of the inner tube D, constituting the other restraining mechanism F' (see FIG. 2). Because of the semicircular shape, the projecting portion 34 of the restraining mechanism F' is disengaged from the recessed portion 29 against the inherent elasticity by depression of the inner tube D, which is therefore movable by the depression. At least one of the restraining F, F' may be provided.

An engaging recessed portion 35 can be formed in the outer peripheral surface of the inner tube D at its upper end for trapping the projecting portion 34 and the pawl 28 of the manual lever 27 when the inner tube D is in the second joined position. This prevents slipping-off of the needle or like trouble during the mixing procedure.

The restraining mechanisms F, F' are not limited specifically in construction insofar as they are capable of usually restraining the inner tube D in the first joined position and releasing the tube D from the restrained position for use.

To hold the joint between the outer tube B and the inner tube D hermetic, the seal ring G is held between the upper end inner periphery of the outer tube B and the outer peripheral surface of the inner tube D, as positioned inside the body 24 of the adapter H.

FIG. 2 shows the medicine container of the present invention during transport or storage.

During transport or storage, the engaging ring 7 provided at the upper end of the socket 6 and in engagement and intimate contact with the annular projection 8 along the outer periphery of top of the opening seal portion 2 and with the top surface of the rubber closure 5 acts as a seal for holding the joint between the container A and the outer tube B hermetic. Further the seal ring G acts to hold the joint between the outer tube B and the inner tube D airtight. Thus, the interior of the outer and inner tubes B, D is held hermetic reliably with safety until use despite the provision of the upper and lower two removable joints.

Furthermore, the inner tube D is held in the first joined position by the restraining mechanisms F, F' and is therefore prevented from moving from the first joined position toward the second joined position even if subjected to an impact during transport or storage. This obviates the likelihood that defectives will occur owing to the movement of the inner tube D.

When the medicine container is to be used, the outward portion 27*b* of the manual lever 27 of the restraining mechanism F is pressed in the direction of arrow 30 shown in FIG. 5, whereupon the inward portion 27*a* opens toward the direction of arrow 32, as supported at the intermediate point 31 for pivotal movement. This movement disengages the pawl 28 on the inner side of outer end of the inward portion 27*a* from the recessed portion 29, releasing the inner tube D from the restraint by the mechanism F. Even if freed from the restraint by the mechanism F, the inner tube D is held restrained by the mechanism F'. However, since the restraining mechanism F' comprises the recessed portion 29 and the projecting portion 34 elastically engaged therein, the inner tube D can be released from the restraint by being depressed with a force exceeding the force of elastic engagement.

When the inner tube D in this state is depressed by a force exceeding the force of elastic engagement of the restraining mechanism F' and thereby moved from the first joined position to the second joined position, the double-ended needle C also moves from the upper position to the lower position as shown in FIG. 7, causing the upper and lower needle members 10, 11 to pierce the opening seal portions 19, 2, respectively, whereby the interior of the container A and the interior of the vial E are made to communicate with each other through the needle members 10, 11. FIG. 7 shows the container A and the vial E as positioned in an inverted arrangement.

Figure 1:
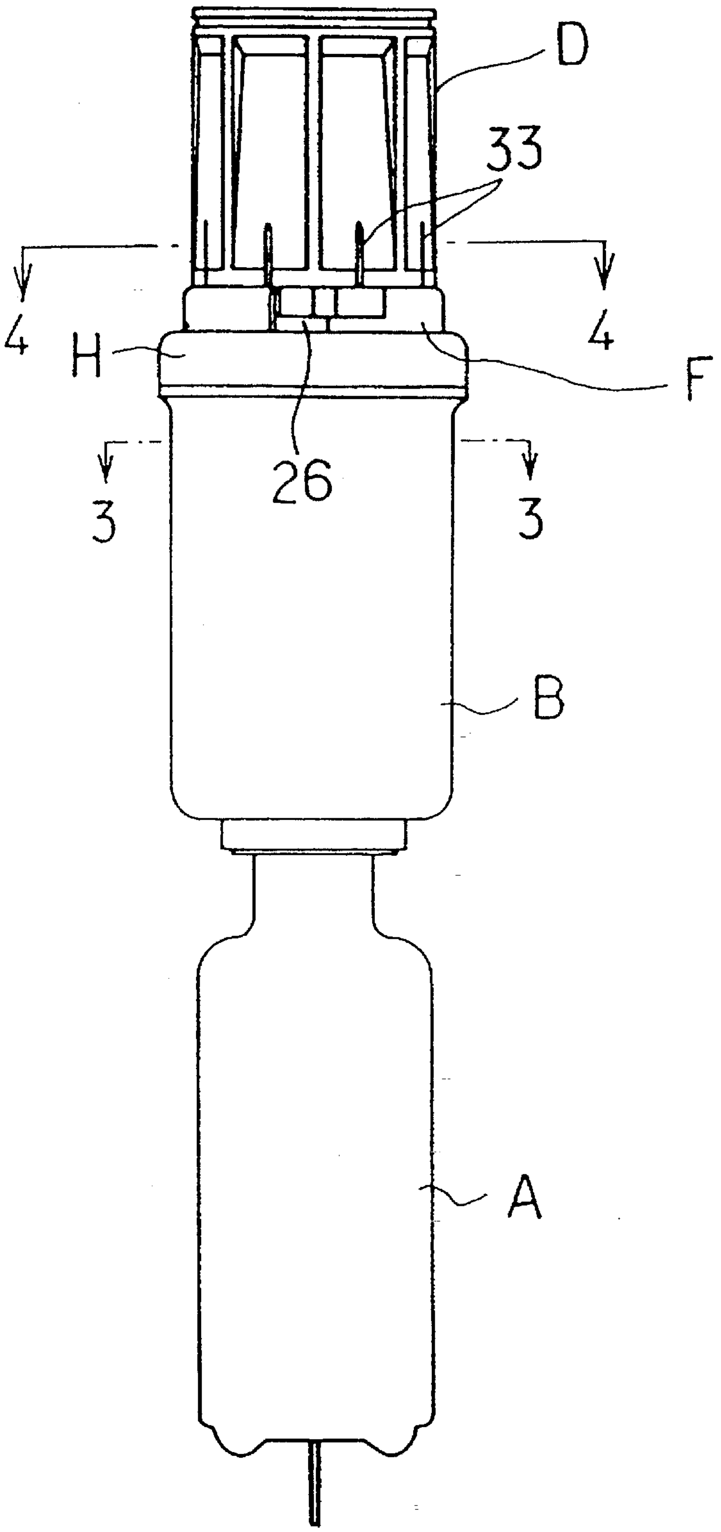
FIG. 1 is a front view showing a first embodiment of the invention in its usual state.
Figure 4:
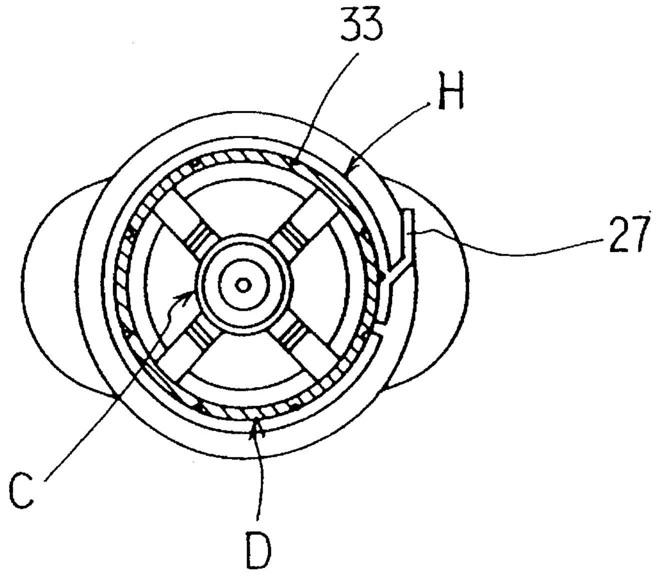
FIG. 4 is a view in section taken along the line 4—4 in FIG. 1.

During the depression of the inner tube D, the internal pressure of the outer and inner tubes B, D rises because the internal volume decreases as the inner tube D is pushed down. Air vent means can be provided to preclude the rise in the internal pressure. Indicated at 33 in FIGS. 1 and 4 are furrows formed in the outer peripheral surface of the inner tube D at its lower portion for releasing air therethrough. The lower ends of the furrows 33 are positioned above the seal ring G shown in FIG. 2 and separated off from the interior of the outer and inner tubes B, D. However, the furrow ends communicate with the interior of the tubes B, D for the escape of air when brought to below the seal ring G by the depressive movement of the inner tube D.

The whole amount of medicine within the vial E can be dissolved in the dissolving liquid 3 by turning the entire medicine container upside down with the interior held in communication as shown in FIG. 7, further deforming the container A by pressure as required to cause the liquid 3 to flow into the vial E through the needle members 10, 11 to dissolve the medicine, inverting the medicine container to the original state to return the medicine solution from the interior of the vial E to the interior of the container A and thereafter repeating the same procedure.

The solution can be prepared rapidly if the seal portions are pierced with the needle with the overall medicine container held inverted from the beginning since the liquid 3 in the container A then falls into the vial E under gravity. In this case, there is a likelihood of the dissolving liquid leaking through the needle member 10 before the needle member 10 pierces the seal portion 19. This can be obviated if the outer end of the needle member 10 is covered with a rubber cap 36 as seen in FIG. 2. The rubber cap 36 preferably has such a thickness that the needle member 10 can readily penetrate through the cap when piercing the seal portion. The outer end of the needle member 11 may also be covered with a rubber cap 37.

As shown in FIG. 7, the projecting ridge 12 and the engaging ring 7 also serve to provide spaces for accommodating the respective rubber caps 36, 37 as pierced.

After completion of the mixing-dissolving procedure, the medicine container can be separated into three portions by removing the outer tube B from the container A and further withdrawing the inner tube D from the outer tube B. Further when required, the medicine container can be separated into five portions by withdrawing the vial E and the double-ended needle C from the inner tube D.

According to the present invention, the socket 6 of the outer tube B is fittingly joined to the seal portion 2 by the illustrated threaded portion 9, which, however, may be replaced, for example, by a projection elastically engageable in a recess.

According to the present invention, examples of medicines to be contained in the vial E can be anticancer preparations, anti-ulcer preparations, steroid preparations, urokinase preparations, vitamin preparations, etc. in addition to antibiotics. Examples of useful dissolving liquids or diluents to be contained in the container A can be distilled water for injection, physiological saline, glucose solution, etc.

FIGS. 8 to 18 show a second embodiment of the present invention. Throughout the accompanying drawings, like parts are designated by like reference numerals or symbols.

Figure 8:
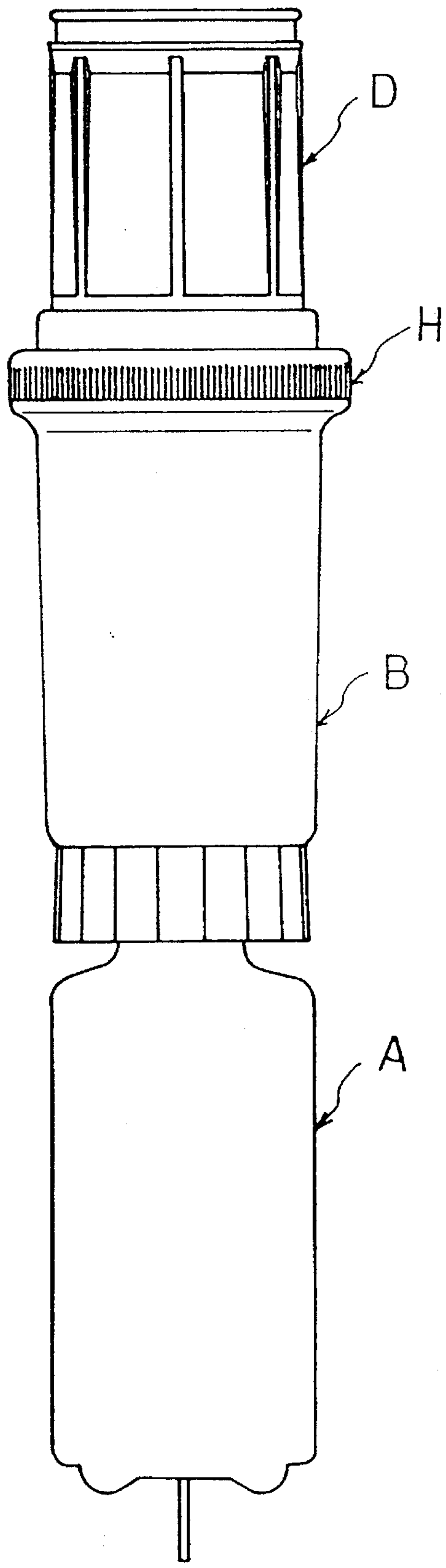
FIG. 8 is a front view showing a second embodiment of the invention in its usual state.
Figure 9:
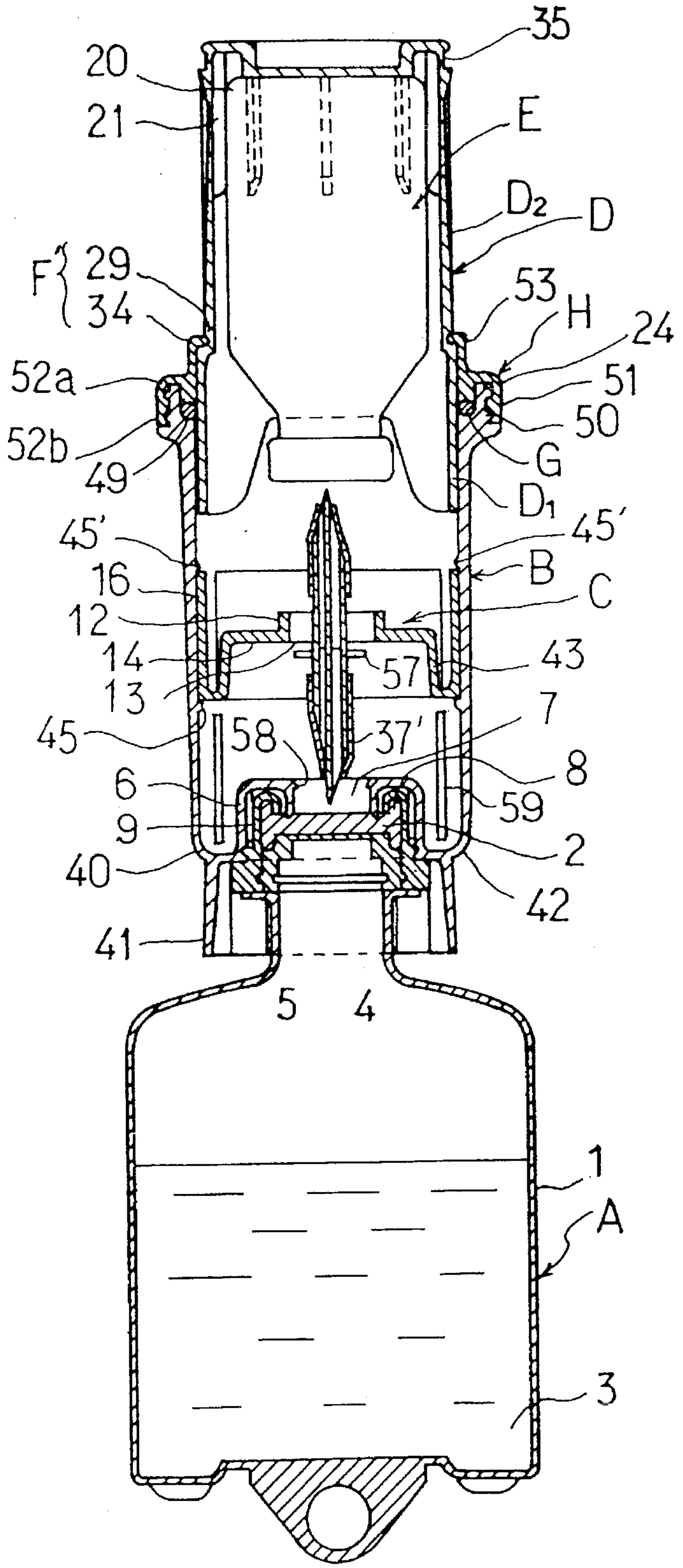
FIG. 9 is a view in vertical section of the same.
Figure 10:
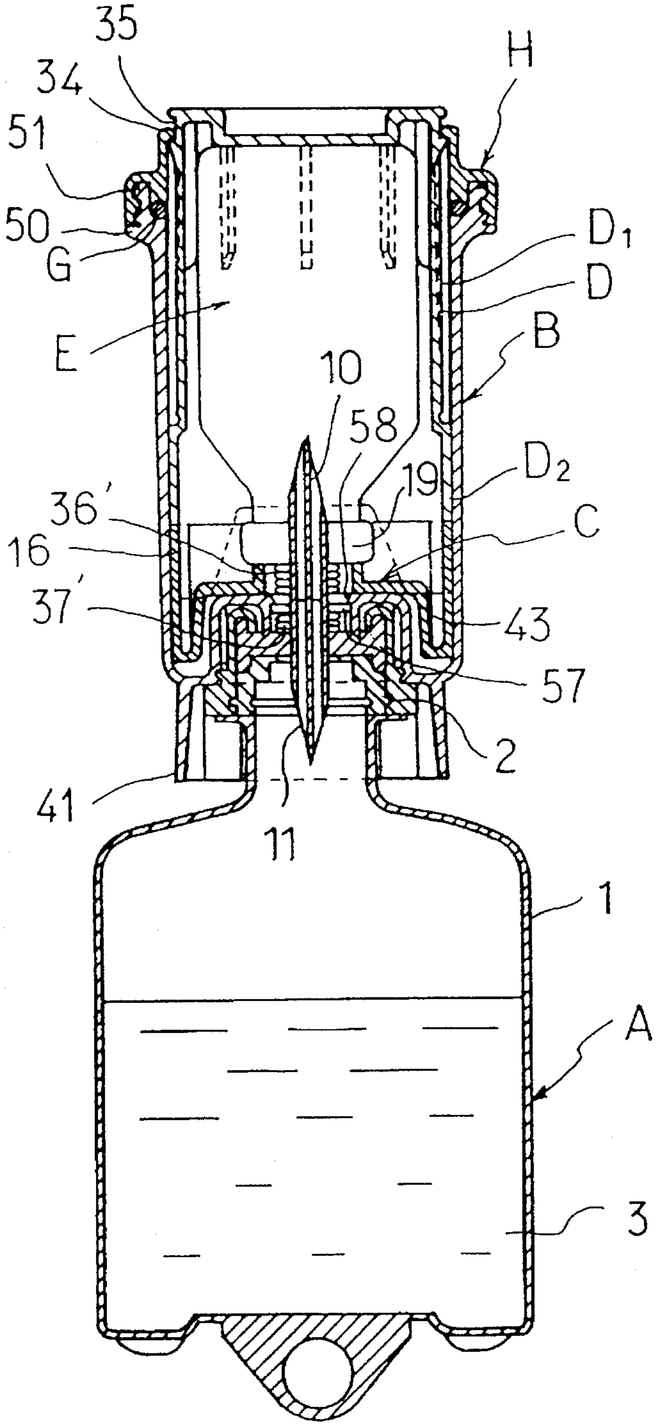
FIG. 10 is a view in vertical section of the same in use.

As will be apparent from the overall views of FIGS. 8 to 10, the second embodiment, i.e., another medicine container, comprises a dissolving liquid container A, outer tube B, double-ended needle C, inner tube D, medicine-containing vial E, restraining mechanism F', seal ring G and adapter H like the first embodiment.

The dissolving liquid container A comprises a body 1 having an open upper end, and an opening seal portion 2 closing the opening.

The body 1 is deformable by pressing and molded of a thermoplastic synthetic resin such as polyethylene or polypropylene resin, and has a dissolving liquid 3 accommodated therein.

The opening seal portion 2 can be composed of an inner closure 4 of plastics attached to the open upper end of the body 1 as by heat sealing, and a rubber closure 5 resembling a cap and fitted over the inner closure 4 as will be apparent from FIG. 9. The opening seal portion 2 is not limited specifically in structure insofar as it permits piercing with a needle member of the double-ended needle C.

The outer tube B is made of plastics and fixedly joined to the seal portion 2 of the container A so as to extend upward from the portion 2 concentrically therewith while holding the needle C therein upwardly and downwardly slidably.

The outer tube B has a socket 6 upwardly projecting from its lower end concentrically therewith as means for fixedly joining the tube to the seal portion 2. When the socket 6 is fastened to the seal portion 2 by being guided by a threaded portion 9, an engagement ring 7 inwardly projecting from the upper end of the socket 6 and inverted L-shaped in section is brought into engagement and intimate contact with an annular projection 8 on the top surface of the seal portion 2 along its outer periphery, with the lower end of the ring 7 pressed against the top surface of the rubber closure 5, whereby a seal is formed to provide an airtight joint. The construction described above is the same as in the first embodiment.

Figure 11:
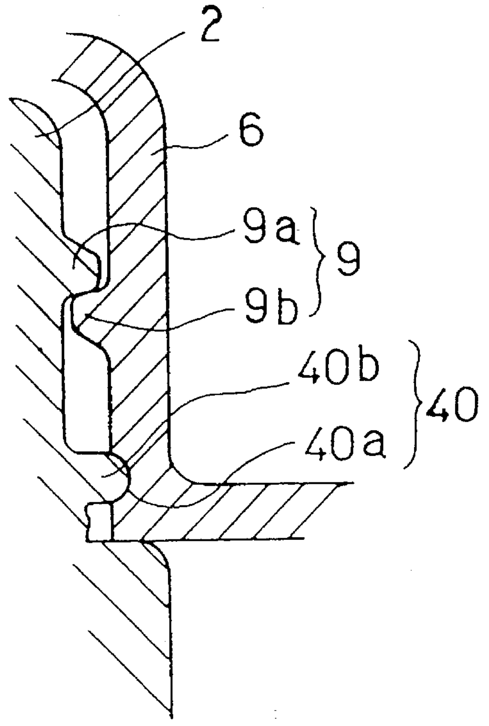
FIG. 11 is a view for illustrating a threaded portion having a lock mechanism.

The second embodiment has threaded means 9 provided with a lock mechanism 40, the construction of which is shown in FIG. 11 on an enlarged scale. The lock means 40 comprises annular recessed and projecting portions *40a*, *40b* elastically engageable with each other owing to the inherent elasticity of plastics immediately before the threaded means 9 is tightened up. The force of elastic engagement between the recessed and projecting portions *40a*, *40b* is made smaller than the force of engagement between the threads *9a*, *9b* of the means 9 so as to facilitate the engagement between the portions *40a*, *40b* utilizing the force of engagement of the threaded means 9.

The lock mechanism 40 functions to prevent the threaded means 9 from loosening by the elastic engagement between the recessed and projecting portions *40a*, *40b*.

The outer tube B has at its lower end a skirt 41. The skirt 41 is concentric with the outer tube B and has a lower end extending to a position slightly beyond the lower end of a lower needle member 11 of the double-ended needle C when the medicine container is in the state shown in FIG. 10 for a mixing-dissolving procedure.

While the outer tube B is removed from the dissolving liquid container A for disposal after the mixing-dissolving procedure has been completed, the lower needle member 11 of the needle C is hazardous if projecting out beyond the lower end of the outer tube B. The skirt 41 is useful as a measure for precluding such a hazard.

To ensure safety, the skirt 41 preferably has the smallest possible outside diameter insofar as it is fittable around the opening seal portion 2 of the liquid container A. A step 42 is provided at the boundary between the skirt 41 and the outer tube B. To render the skirt 41 fittable around the seal portion 2, the skirt 41 can be so tapered as to flare downward. The skirt 41 can be held with fingers easily when the outer periphery thereof has many sides, e.g., 18 sides. The skirt 41 is then convenient to use as a portion for rotating the outer tube B.

The double-ended needle C is made of plastics and comprises a pair of upper and lower needle members 10 and 11 communicating with each other. The needle members 10, 11 are fixed to a disklike needle holder 13 reinforced with an upwardly projecting ridge 12 and are aligned with the center axis of the holder. The needle holder 13 has a plurality of arms radially extending from the outer periphery thereof, for example, six arms 14 arranged at a spacing of 60 degrees (see FIG. 12). A slider 16 which is circular-arc when seen from above is provided for every two arms 14, as attached to the outer arm ends by spring portions 43. The sliders 16, 16 are spaced apart by a clearance 44.

Figure 12:
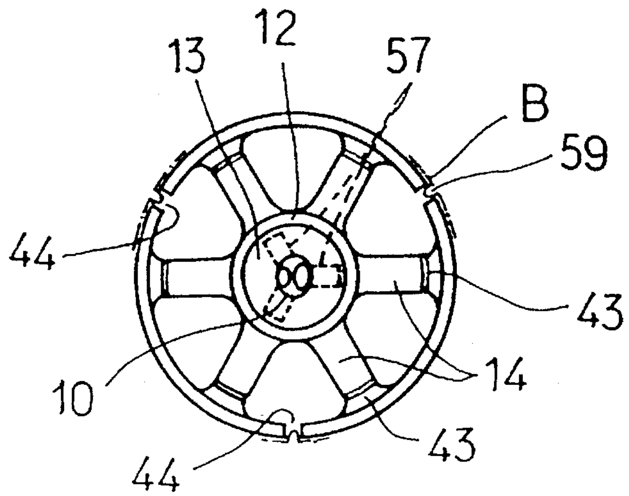
FIG. 12 is a plan view of a double-ended needle included in the second embodiment.
Figure 13:
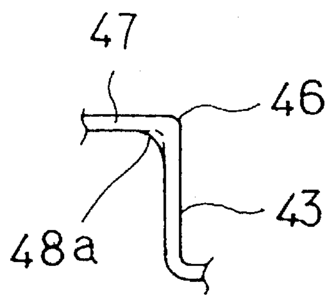
FIG. 13 is a view showing a rib as formed on the needle.

As shown in FIG. 12, the needle C, when in a free state, has an outside diameter slightly larger than the inside diameter of the outer tube B. The outside diameter of the needle C can be reduced by forcing the sliders 16 toward the center of the needle against the spring portions 43.

The needle C is inserted, as diametrically contracted by compressing the spring portions 43, into the outer tube B. When the needle is thus inserted, the spring portions 43 act to press the sliders 16 against the inner surface of the outer tube B to produce a force of frictional engagement at the portions of contact between the outer tube B and the sliders 16. The needle can be held at a desired inserted position inside the outer tube B by the force of frictional engagement.

The needle C is slidable upward and downward within the outer tube B. To render the needle C slidable as centered with the tube B, the sliders 16 have a relatively large vertical width which is usually about 12 to about 25 mm. To enable three sliders 16 to collectively cover approximately the entire range of 360 degrees, each slider 16 has an angular width of about 120 degrees. When the medicine container is in the state shown in FIG. 9 before use, the needle C inserted in the outer tube B is held in an upper position within the tube B by the force of frictional engagement produced at the contact portions of the sliders 16 and the outer tube B. To hold the needle in this position more effectively, stoppers 45', 45 can be provided on the inner surface of the outer tube B at upper and lower portions thereof, respectively.

The medicine container is transported as assembled in the state shown in FIGS. 8 and 9. If the upper needle member 10 or the lower needle member 11 of the needle C strikes against the rubber surface of opening seal portion 19 of the vial E or the rubber surface of opening seal portion 2 of the dissolving liquid container A owing to an impact exerted on the needle during transport, there is a likelihood that an extraneous matter will be produced on the rubber surface to further distort the needle end. This likelihood can be obviated by restraining the needle C in the upper position (see FIG. 9) below the seal portion 19 and above the rubber closure 5 as stated above.

Figure 14:
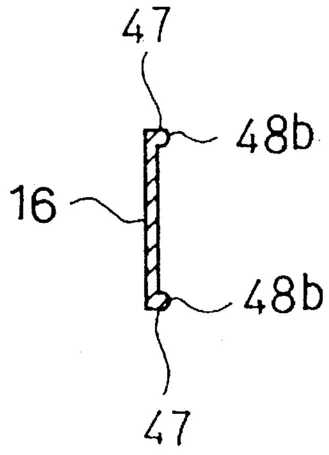
FIG. 14 is a view showing other ribs as formed on the same.

To prevent the distortion of the needle C due to molding shrinkage, reinforcing ribs 48*a*, 48*b* can be formed at the junction 46 between the arm 14 and the spring portion 43 on the inner side thereof (see FIG. 13), and at the upper and lower edges 47, 47 of the slider 16 on the inner side thereof (see FIG. 14).

The inner tube D is made of plastics and has a closed upper end. The tube is slidably fitted in the outer tube B through an open upper end thereof so as to be movable from a first joined position of shallow fit (see FIG. 9) to a second joined position of deep fit (see FIG. 10).

The inner tube D is formed in a lower portion of its outer peripheral surface with an annular lower engaging recessed portion 29 which is a component of the restraining mechanism F'. The recessed portion 29 is positioned above the upper end of the outer tube B when the inner tube D is in the first joined position shown in FIG. 9.

The inner tube D comprises a large diameter portion D1 below the recessed portion 29 and a small diameter portion D2 above the portion 29. The tube D has its large diameter portion D1 slidably inserted in the outer tube B. A small clearance is formed in the tube B around the small diameter portion D2 when this portion D2 is inserted.

As shown in FIG. 9, the medicine-containing vial E is fixedly but removably held in an inverted state in the inner tube D with an opening seal portion 19 of the vial directed downward. The vial is fixedly held to the inner tube by suitable means. With reference to FIG. 9, a multiplicity of platelike engaging rims 21 integral with the inner tube D are formed on the inner peripheral surface of upper portion of the tube D defining an insertion space 20 as in the first embodiment, such that the lower portion of the vial E is forced into the space 20 against the inherent elasticity of the rims 21. The rims 21 can be inclined so as to be given improved ability to hold the vial E. The opening seal portion 19 of the vial E comprises, for example, a rubber closure to permit piercing with the double-ended needle C.

The joint between the inner and outer tubes B and D has a rubber seal ring G for holding the joint airtight.

The seal ring G is accommodated in a recess 49 in the upper end of the outer tube B, as tightly fitted around the large diameter lower portion D1 of the inner tube D.

The adapter H is used for the joint between the outer and inner tubes B, D for fixedly enclosing the seal ring G in the recess 49.

The adapter H has a lower portion in the form of a double tube comprising an outer tubular portion 52*a* and an inner tubular portion 52*b*. The outer tubular portion 52*a* is fastened to the outer side of the upper end of the outer tube B by threaded means 51 having a lock mechanism 50. The inner tubular portion 52*b* is fitted in the recess 49 to fixedly enclose the seal ring G in the recess 49. The lock mechanism 50 and the threaded means 51 are the same as the lock mechanism 40 and the threaded means 9, respectively, in construction which are shown in FIG. 11.

Figure 15:
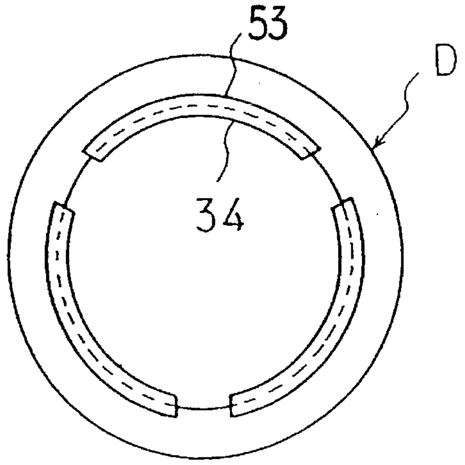
FIG. 15 is a plan view of an adapter in the same embodiment.

The adapter H has a tubular upper portion indicated at 53 and slidably covering the outer periphery of large diameter lower portion D1 of the inner tube D. The upper tubular portion 53 is provided at its upper end with an engaging inwardly projecting portion 34 serving as another component of the restraining mechanism F'. The projecting portion 34 engages in the recessed portion 29 at the lower end of small diameter portion D2 of the inner tube D, holding the inner tube D in the first joined position of shallow fit. The engaging projecting portion 34, if extending continuously over the entire range of 360 degrees, will not be easily released from the engaging recessed portion 29, so that the upper tubular portion 53 is divided into three segments as shown in FIG. 15.

FIG. 9 shows the medicine container of the invention in a state for transport or storage.

During transport or storage, the engagement ring 7 provided at the upper end of the socket 6 and in engagement and intimate contact with the annular projection 8 along the outer periphery of top of the opening seal portion 2 and with the top surface of the rubber closure 5 acts as a seal for holding the joint between the container A and the outer tube B airtight. This airtightness is enhanced by the function of the lock mechanism 40 provided for the threaded means 9 as a seal. Further the seal ring G acts to hold the joint between the outer tube B and the inner tube D airtight. Consequently, the interior of the outer and inner tubes B, D is held airtight reliably with safety until use despite the provision of the upper and lower two removable joints.

Moreover, the lock mechanisms 40, 50 function to prevent the threaded means 9, 51 from loosening, so that the threaded means 51, 9 of the upper and lower joints are unlikely to loosen, holding the components joined together by screw-thread engagement reliably with safety until use.

Additionally, the inner tube D is held in the first joined position by the restraining mechanism F' and is therefore prevented from moving from the first joined position toward the second joined position even if subjected to an impact during transport or storage.

When the inner tube D is depressed from the state shown in FIG. 9 for use, the depressive force brings the recessed and projecting portions 29, 34 of the restraining mechanism F' out of elastic engagement with each other, consequently moving the inner tube D from the first joined position toward the second joined position. In the initial stage of the downward movement, the outer peripheral surface of lower portion D1 of the inner tube D is in pressing contact with the seal ring G because of the large outside diameter to produce a great force of frictional resistance, necessitating a great depressing force. When the small diameter upper portion D2 is brought to the position of the seal ring G with the downward movement of the large diameter portion D1, the reduction in the outside diameter markedly diminishes the frictional resistance offered by the seal ring G to reduce the depressing force thereafter needed. Thus, the procedure for pushing down the inner tube D requires a great depressing force only in the initial stage of the procedure, after which the tube can be pushed down easily with a small force. The present container can therefore be handled with greater ease. The inner tube D can be pushed down with one hand, with the skirt 41 at the lower end of the tube B held with the other hand.

During the depression of the inner tube D, the internal air pressure of the outer and inner tubes B, D rises as the inner tube D is pushed down. According to the present embodiment, after the small diameter portion D2 has reached the position of the seal ring G with the depression of the inner tube D, the seal ring G functions as a seal to a lesser extent or no longer functions as such, consequently permitting escape of air. To initiate venting earlier, the upper end of large diameter portion D1 of the inner tube D can be formed with vent recesses 54 in its inner peripheral surface.

Upon the inner tube D moving from the first joined position shown in FIG. 9 to the second joined position shown in FIG. 10, the double-ended needle C moves from the upper position shown in FIG. 9 to the lower position shown in FIG. 10 by being pushed by the opening seal portion 19 of the vial E. This movement causes the upper and lower needle members 10, 11 of the needle C to pierce the seal portion 2 of the dissolving liquid container A and the seal portion 19 of the vial E, respectively, whereby the interior of the container A and the interior of the vial E are made to communicate with each other via the needle members 10, 11.

To enable the needle C to move inside the outer tube B as centered with the tube B, the outer tube B can be slightly tapered. The taper of the outer tube B causes the spring portions 43 included in the arms 14 of the needle C to exert a force which increases with the descent of the needle, gradually increasing the force of frictional engagement between the outer tube B and the sliders 16 and consequently permitting the needle C, accordingly the upper and lower needle members 10, 11, to move inside the outer tube B without inclination. The needle members 10, 11 thus centered with improved accuracy pierce the respective seal portions 19, 2 centrally of their rubber closures accurately and reliably.

In the state shown in FIG. 10 wherein the liquid container A is internally in communication with the vial E through the upper and lower needle members 10, 11, the engaging projecting portion 34 of the restraining mechanism F' is in engagement with an engaging recessed portion 35 in the upper end of outer periphery of the inner tube D, holding the inner tube D in its depressed position. Since the height of the vial E involves a tolerance, it is desirable that the recessed portion 35 have an increased vertical width which is, for example, about twice the vertical width of the projecting portion 34 so as to correct or accommodate this tolerance.

The whole amount of medicine within the vial E can be dissolved in the dissolving liquid 3 by inverting the entire medicine container in the state shown in FIG. 10 wherein the component containers are in communication as shown in FIG. 10, further deforming the container A by pressure as required to cause the liquid 3 to flow into the vial E through the needle members 10, 11 to dissolve the medicine, inverting the medicine container to the original state to return the medicine solution from the vial E to inside the container A and thereafter repeating the same procedure.

The solution can be prepared rapidly if the seal portions are pierced with the needle with the overall medicine container held inverted from the beginning since the dissolving liquid 3 in the container A then falls into the vial E under gravity. In this case, there is a likelihood of the dissolving liquid 3 leaking through the needle member 10 before the needle member 10 pierces the seal portion 19. This can be precluded if the outer end of the needle member 10 is covered with a rubber cap 36' as shown in FIG. 9.

Figure 17:
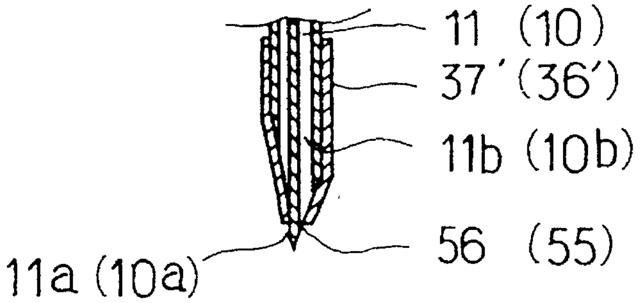
FIG. 17 is a view for illustrating a rubber cap as fitted to a needle member of the same.

With reference to FIG. 17, the rubber cap 36' has a small insertion hole 55 in its top end, with the tip 10*a* of the needle member 10 projecting from the hole 55. When the rubber cap 36' is fitted around the needle member 10, the outer open end 10b of the needle member 10 is closed with the rubber cap 36'. This obviates the likelihood of the liquid leaking.

When the seal portion 2 is pierced with the needle member 10, on the other hand, the rubber cap 36' is rolled up onto the base portion of the needle member 10 as seen in FIG. 10, permitting passage of the liquid.

A rubber cap 37' of the same construction as the rubber cap 36' may be attached to the other needle member 11.

The rubber caps 36', 37' covering the needle members 10, 11 eliminate the problem of leakage of the contents regardless of which of the seal portions of the vial E and the liquid container A is pierced first. Although piercing in a predetermined order requires a complex control mechanism, the provision of the rubber caps 36', 37' over the needle members 10, 11 eliminates the need to predetermine the piercing order.

Furthermore, the small insertion holes 55, 56 formed in the top ends of the respective rubber caps 36', 37' make it easy to fit the caps to the needle members 10, 11 properly and reliably, obviating the likelihood that the liquid will fail to pass through the needle owing to improper fitting.

During the procedure for dissolving the medicine within the vial E, it is desired that the solution being prepared be checkable visually readily. According to the second embodiment, the inner peripheral surface of the outer tube B is not formed with any indentation or projection that will cause irregular reflection. This enables the user to visually check the solution easily.

After the mixing-dissolving procedure has been completed, the container A is removed from the outer tube B and used as it is for drip infusion. The remaining unit can be separated into parts, which are to be handled individually for disposal.

Among these parts, the double-ended needle C have the needle members 10, 11, which are hazardous if projecting as left exposed. It is therefore desired that the medicine container be separable into parts with the needle C remaining inside the outer tube B.

For this purpose, the outer tube B can be provided in the vicinity of its joint to the dissolving liquid container with a mechanism for retaining the double-ended needle C. The needle retaining mechanism comprises a plurality of retaining pieces 57 extending radially from the upper end of the lower needle member 11 of the needle C. With the inner tube D in its depressed position shown in FIG. 10, the retaining pieces 57 are in engagement with an annular ridge 58 formed at the upper end of the engagement ring 7 at the lower end of the outer tube B, whereby the needle C is locked in its lower position (see FIG. 10), as held to the outer tube B.

To disassemble the unit, the adapter H in the state shown in FIG. 10 is rotated reversely, whereby the inner tube D is freed from the restraint by the outer tube B and rendered withdrawable from the outer tube B. The vial E within the inner tube D is withdrawn along with the inner tube D, or remains, as released from the inner tube D, in the outer tube B depending on the relationship between the resistance of the seal portion 19 thereof to withdrawal of the needle and the retention of the vial by the inner tube D, whereas the unit can be separated free of trouble in either case.

Figure 16:
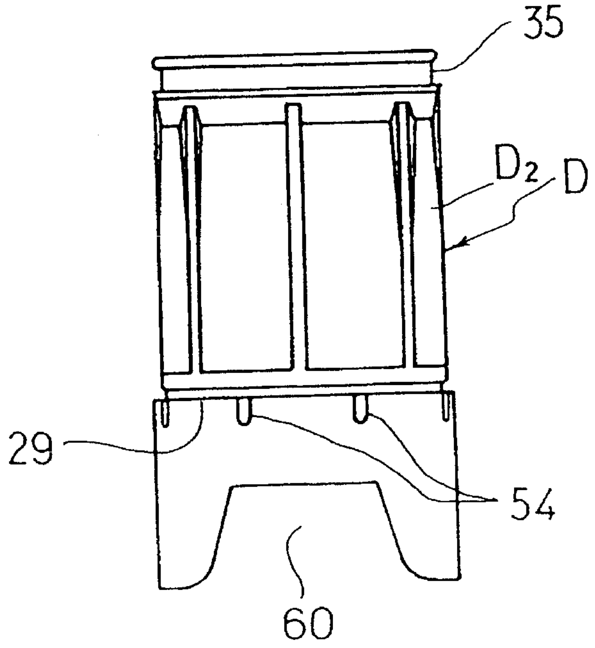
FIG. 16 is a front view of an inner tube of the same.

For example as shown in FIG. 16, a cutout 60 is formed in the large diameter lower portion D1 of the inner tube D for the user to readily pick up the vial E within the inner tube D for removal.

On the other hand, in the case where the vial E remains in the outer tube B, it is convenient to withdraw the vial while rotating the vial so as to reduce the resistance of the seal portion to the slipping-off of the needle. To prevent the needle C from rotating with the vial E, the needle C can be held against rotation, for example, by linear ribs 59 (see FIG. 9) extending vertically and formed on the inner peripheral surface of lower portion of the outer tube B. The ribs 59 engage in the clearances 44 between the sliders 16 of the needle C to prevent the rotation of the needle C. The needle as thus prevented from rotation is schematically shown in FIG. 12.

Figure 18:
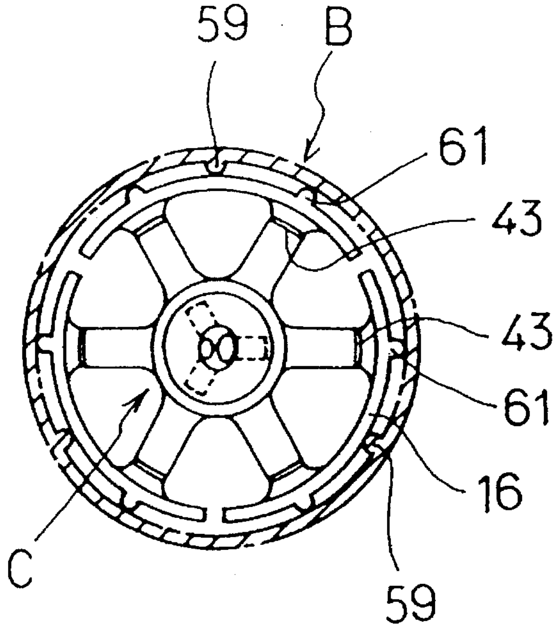
FIG. 18 is a plan view showing a modified double-ended needle.

As shown in FIG. 18, projections 61 may be formed on the outer surface of each slider 16 of the needle C for the rib 59 to engage the projection 61. The projections 61, if provided, deform the spring portions 43 by compression to a greater extent to enhance the force of frictional engagement between the inner peripheral surface of the outer tube B and the sliders.

When the vial E is to be withdrawn from the outer tube B, the resistance of the seal portion 19 of the vial E to the slipping-off of the needle C is smaller than the force of engagement between the needle C and the outer tube B, i.e., between the retaining pieces 57 and the annular ridge 58, with the result that the needle C remains as it is in its lower position inside the outer tube B although the vial E is withdrawn.

The skirt 41 provided at the lower end of the outer tube B eliminates the likelihood of the needle members 10, 11 of the needle C projecting out as exposed, rendering the outer tube B serviceable as a protective case for the needle C.

The outer tube B and the needle C are each made of plastics and can be disposed of as combined together without entailing any particular problem.

ADVANTAGES

The medicine container of the present invention has the following advantages.

(i) During transport or storage, the inner tube is firmly held in the first joined position by the restraining mechanism and is therefore unlikely to move or slip off even if subjected to impact or vibration.

(ii) The interior of the inner and outer tubes can be held airtight reliably with safety because the joints are sealed off and also because the tubes are made of plastics, have great strength and will not break.

(iii) The medicine container is usable merely by slidingly pushing down the inner tube as freed from restraint. This ensures a greatly facilitated mixing-dissolving procedure.

(iv) The medicine container is simple in structure, smaller in the number of components and therefore less costly to manufacture.

(v) The medicine container can be readily disassembled after use and are accordingly disposable as separated into individual parts.

We claim:

1. A medicine container comprising:

(a) a dissolving liquid container having an opening seal portion at an upper end thereof, (b) an outer tube removably hermetically joined and secured to the opening seal portion of the dissolving liquid container so as to extend upward from the opening seal portion concentrically therewith, (c) a double-ended needle fitted in the outer tube and slidable upward and downward, the needle fitted to be held in an upper position above the opening seal portion and movable from the upper position to a lower position to pierce the seal portion for use, (d) an inner tube slidably fitted in the outer tube through an open upper end thereof and fitted to be held in a first joined position of shallow fit, the inner tube being movable from the first joined position to a second joined position of deep fit for use, (e) a medicine-containing vial removably fixed in an inverted state in the inner tube with an opening seal portion of the vial directed downward, the vial being positioned above the needle in the upper position when the inner tube is in the first joined position and movable with the movement of the inner tube to a position where the opening seal portion of the vial is pierced by the needle in the lower position when the inner tube moves to the second joined position, (f) restraining means provided in a joint between the outer tube and the inner tube for restraining the inner tube in the first joined position relative to the outer tube and releasing the inner tube from the restrained position for use in the second joined position, and (g) a seal ring provided in the joint between the outer tube and the inner tube for holding the joint hermetic.

2. A medicine container as defined in claim 1 wherein the joint between the inner tube and the outer tube is provided with a tubular adapter, the adapter being provided with the restraining means for restraining the inner tube in the first joined position relative to the outer tube and releasing the inner tube from the restrained position for use in the second joined position, and the restraining means comprises at least one of a restraining mechanism comprising elastically engageable projecting and recessed portions, and another restraining mechanism comprising a manual lever having a pawl and openable against inherent elasticity, and a retaining groove for the lever pawl to engage in.

3. A medicine container as defined in claim 1 wherein the double-ended needle comprises an upper needle member and a lower needle member, and at least the needle member closer to the vial opening seal portion has attached thereto a rubber cap pierceable with the needle member.

4. A medicine container as defined in claim 3 wherein the rubber cap has a piercing hole formed therein.

5. A medicine container as defined in claim 1 wherein the outer tube is provided at a lower end thereof with a skirt surrounding and spaced apart from the opening seal portion of the dissolving liquid container.

6. A medicine container as defined in claim 1 wherein the inner tube comprises a lower portion having an outside diameter approximately equal to the inside diameter of the outer tube, and an upper portion having an outside diameter slightly smaller than the inside diameter of the outer tube, the lower portion being positioned inside the outer tube, and the inner tube has a stepped portion provided by the difference in diameter between the lower and upper portions and unwithdrawably held to the inner side of the upper end of the outer tube.

7. A medicine container as defined in claim 1 wherein the inner tube is formed at a bottom portion thereof with vial engaging rims inclined toward a circumferential direction in section.

8. A medicine container as defined in claim 2 wherein an adapter is joined to the outer tube, and at least one of the adapter joint and the joint between the outer tube and the liquid container opening seal portion includes threaded means having a lock mechanism.

9. A medicine container as defined in claim 1 wherein the outer tube is provided in the vicinity of its joint to the liquid container with a mechanism for retaining the double-ended needle.

10. A medicine container as defined in claim 1 wherein the double-ended needle has at its center a pair of upper and lower needle members communicating with each other, the needle members being secured to a disklike needle holder and aligned with the center axis thereof, and the needle holder has arms extending radially outward from the outer periphery thereof, each of the arms being provided with a slider circular arc when seen from above, each of the arms including an intermediate spring portion deformable toward the center of the needle by compression.

11. The medicine container of claim 1, further comprising:

means for joining said outer tube and said opening seal portion of the dissolving liquid container to allow the outer tube to remain joined and secured to the opening seal portion during mixing and dissolving a medicine with a dissolving liquid, and be removed from the opening seal portion after the completion of the mixing and dissolving operation so as to use the opening seal portion as an outlet for a medicine solution.

12. The medicine container of claim 11, wherein said opening seal portion includes a rubbery closure.

* * * * *